United States Patent [19]
Khachaturian et al.

[11] Patent Number: 5,265,476
[45] Date of Patent: Nov. 30, 1993

[54] TENSION LOAD TESTING MACHINE

[75] Inventors: Jon E. Khachaturian; Christopher R. Steinmetz, both of New Orleans, La.

[73] Assignee: Versabar, Inc., Harvey, La.

[21] Appl. No.: 834,617

[22] Filed: Feb. 12, 1992

[51] Int. Cl.[5] .............................................. G01N 3/08
[52] U.S. Cl. ......................................... 73/828; 73/840
[58] Field of Search ................. 73/828, 826, 830, 834, 73/837, 158

[56] References Cited

U.S. PATENT DOCUMENTS

| | | | |
|---|---|---|---|
| 2,389,912 | 11/1945 | Jacoel | 73/837 X |
| 2,533,025 | 12/1950 | Martin | 73/837 |
| 3,010,311 | 11/1961 | Meldrum et al. | 73/828 |

OTHER PUBLICATIONS

Yarbrough Cable Service Inc., Rigging Supplies Brochure.

*Primary Examiner*—Jerry W. Myracle
*Attorney, Agent, or Firm*—Pravel, Hewitt, Kimball & Krieger

[57] ABSTRACT

A testing device for testing lifting equipment and accessories such as slings, shackles and the like has a longitudinally extending frame with left and right sides, each parallel to the other and to rails positioned between the frame sides. Moving carriages travel the rails to a desired position apart, such as for testing a sling of a certain length. The carriages have retractable bearing members that can engage the frame, enabling each carriage to anchor its position for testing. Sets of powered rams move the carriages apart when an accessory to be tested is attached at its ends to the two carriages. The rams are sized so that the first set has greater travel for initial stretching while the second set has higher loading capability for high end loading after stretching.

22 Claims, 4 Drawing Sheets

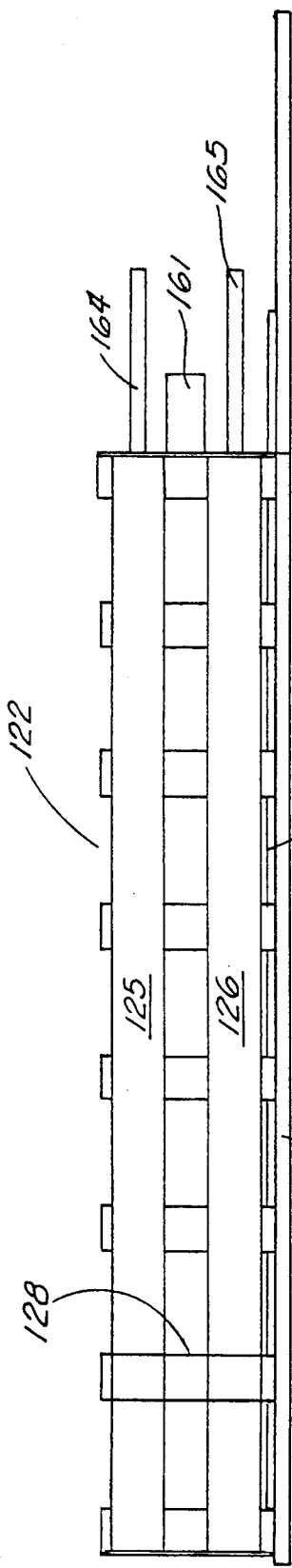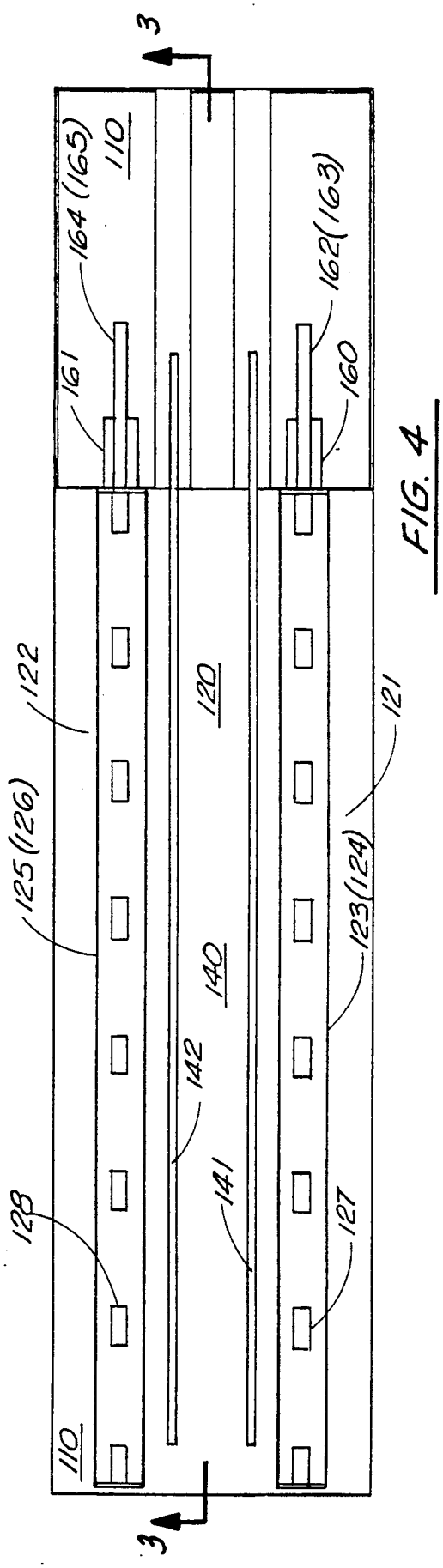

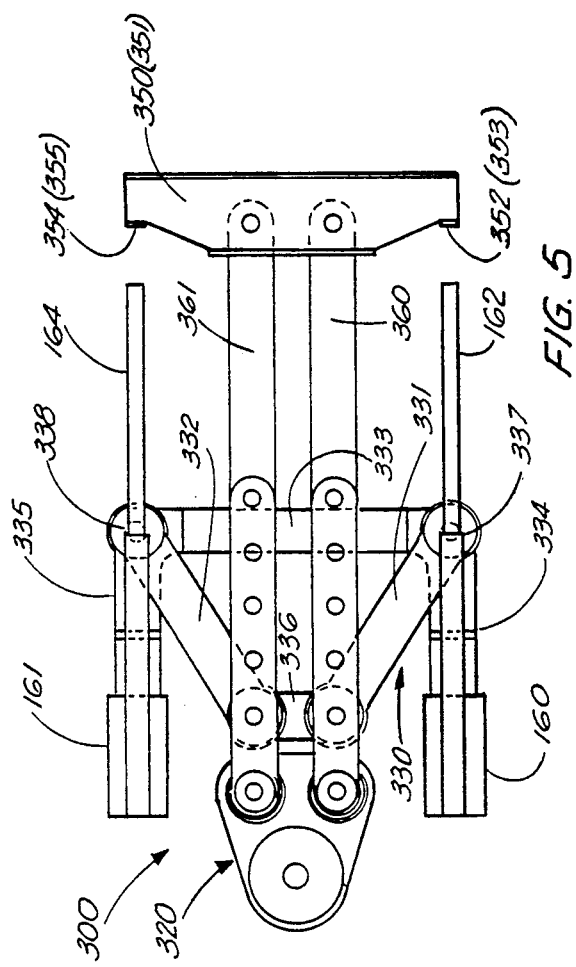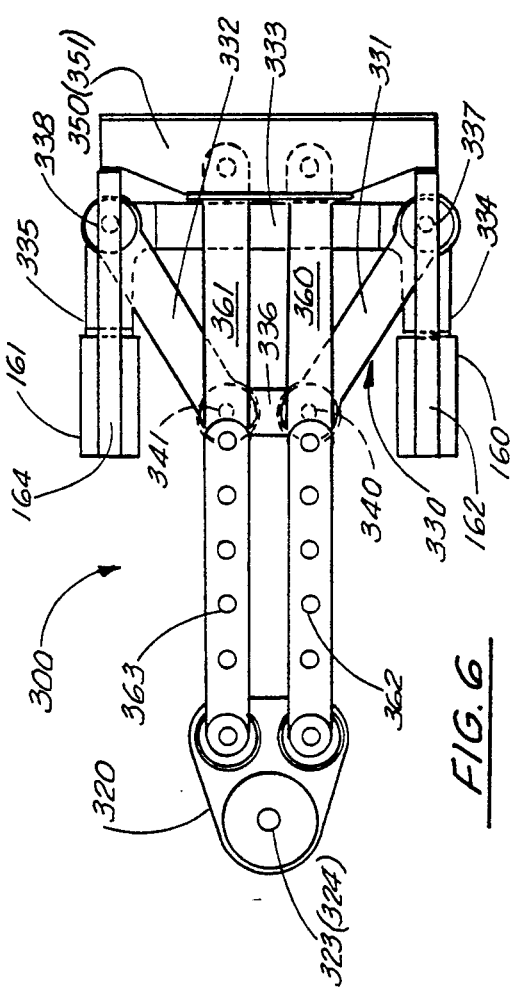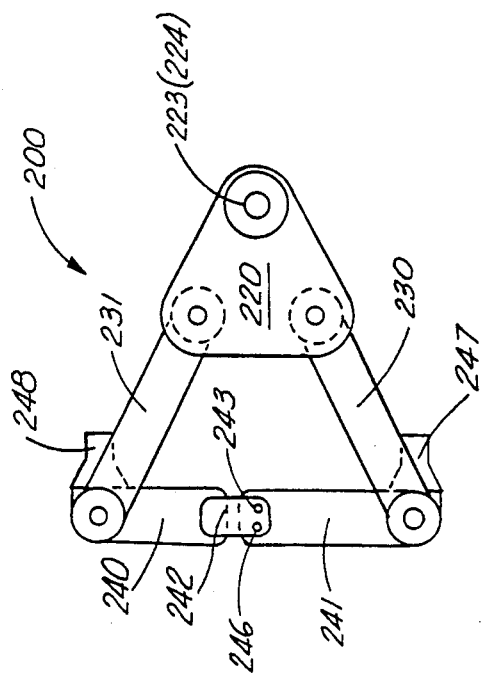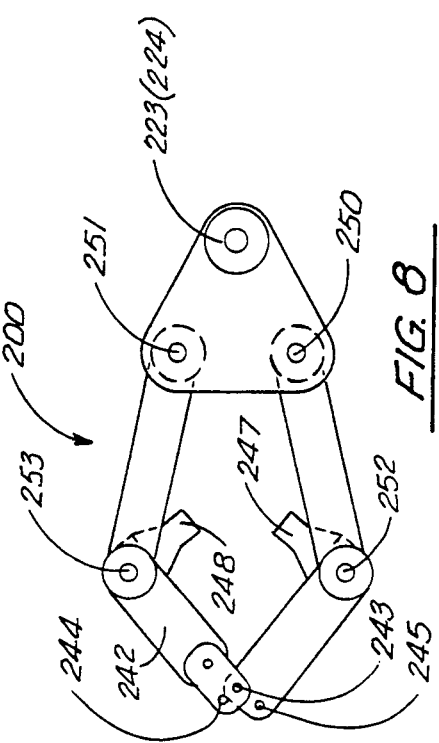

TENSION LOAD TESTING MACHINE

BACKGROUND OF THE INVENTION

2. Field of the Invention

The present invention relates to machines for load testing lifting accessories, lifting equipment, and other tension carrying devices, and more particularly relates to an improved tension load testing machine that can adjust to fit the length of the accessory being tested in both stretched and relaxed positions, and wherein loading preliminarily stretches the accessory and thereafter tests load capability up to several thousand tons.

1. General Background

In various fields of construction and technology, heavy cranes, draglines, booms and like lifting devices are used for fabrication, construction and installation purposes. An example is the offshore oil and gas industry wherein large pre-fabricated oil rigs, platforms and production equipment are constructed in a fabrication yard and then lifted for placement on a site offshore.

In the petrochemical industry, cranes lift large vessels and prefabricated packages of several hundreds or thousands of tons. In the marine industry, large boats are lifted using cranes and the like.

Each of the various lifting environments normally involves a "package" to be lifted that is worth a great deal of money. Several millions of dollars can be lost if a large package is dropped or damaged during a lift. Typically, lifting accessories such as slings, shackles, and rigging are rated for a given load. However, it would be desirable to know that a sling, shackle, or like lifting accessory did in fact have the ability to actually hold a given load. This is especially true of older accessories that have been subjected to numerous loadings already.

One commercial machine used for loading, testing, or "proof loading" is described in brochures of Yarbrough Cable Service, Inc. of Memphis, Tenn. The Yarbrough machine is described in the Yarbrough brochure as being able to proof load to three million pounds (3,000,000) and up to two hundred feet (200') in length. The Yarbrough device employs hydraulic cylinders, and an elongated structural frame having longitudinal and transverse beam portions.

SUMMARY OF THE PRESENT INVENTION

The present invention provides an improved testing device that allows lifting accessories of different lengths to be easily tested even when the accessory stretches significantly upon loading.

The present invention provides an improved testing device that has utility in the testing of tensile load carrying members such as wire rope slings and the like.

The present invention features a pair of carriages to which the ends of a load carrying accessory are attached and wherein the position of the carriages can be adjusted into desired locations before testing.

The present invention features first and second loading systems that enable the accessory being tested to be preliminarily stretched until maximum loading is approached and wherein the second loading system can load the accessory at or near the rated capacity of the accessory.

The present invention features connecting ends in a truss configuration which facilitate handling and reduce material costs.

BRIEF DESCRIPTION OF THE DRAWINGS

For a further understanding of the nature and objects of the present invention, reference should be had to the following detailed description taken in conjunction with the accompanying drawings, in which like parts are given like reference numerals, and wherein:

FIG. 3 is a partial sectional elevational view at the apparatus centerline of the preferred embodiment of the apparatus of the preset invention;

FIG. 4 is a partial top view of the preferred embodiment of the apparatus of the present invention;

FIG. 5 is a top fragmentary view of the preferred embodiment of the apparatus of the present invention fully extended;

FIG. 6 is a top fragmentary view of the preferred embodiment of the apparatus of the present invention in retracted position;

FIG. 7 is a top fragmentary view of the preferred embodiment of the apparatus of the present invention showing the loading configuration;

FIG. 8 is a top fragmentary view of the preferred embodiment of the apparatus of the present invention showing the travelling configuration.

DETAILED DESCRIPTION OF THE PREFERRED EMBODIMENT

Figure 1:
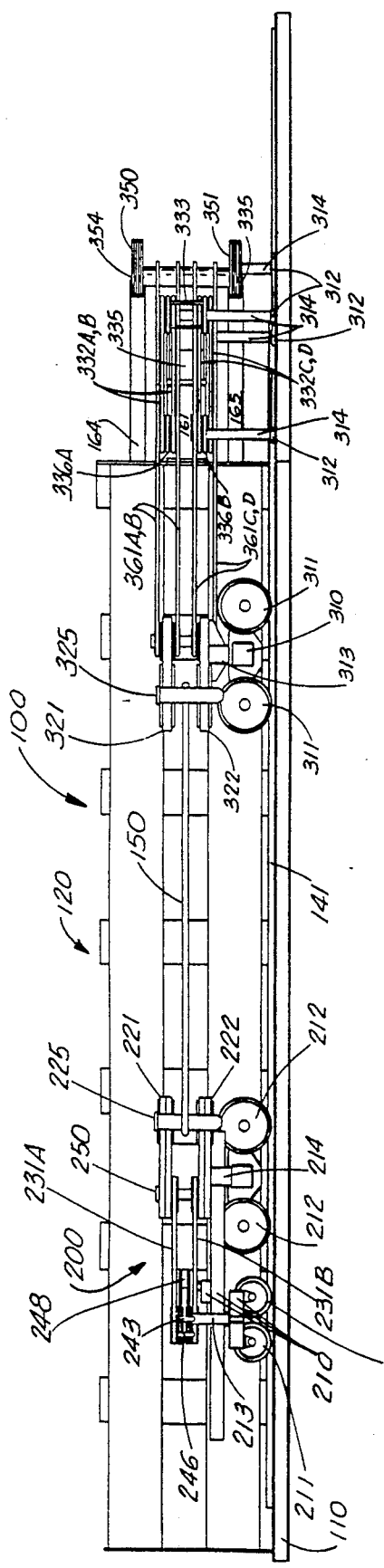
FIG. 1 is a sectional elevational view at the apparatus center line of the preferred embodiment of the apparatus of the present invention.

FIGS. 1-4 illustrate generally the preferred embodiment of the apparatus of the present invention designated generally by the numeral 100. The testing apparatus 100 of the present invention is typically set upon a firm underlying support such as pad foundation 110 which can be, for example, a thick reinforced concrete slab.

Testing apparatus 100 includes an elongated structural frame 120 (eg. welded structural steel) including left and right side portions 121, 122 respectively. Frame 120 includes a plurality of elongated horizontal compression members, each preferably tubular in form, are designated generally by the numerals 123-126. The right frame 122 includes a plurality of vertically extending right box girder stop members 128 which extend through compression members 125, 126 while the left side frame 121 includes a plurality of vertically extending left side box girder stop members 127 extending through members 123, 124 (Each box girder 127, 128 extends to foundation 110 to support frames 121, 122).

Figure 2:
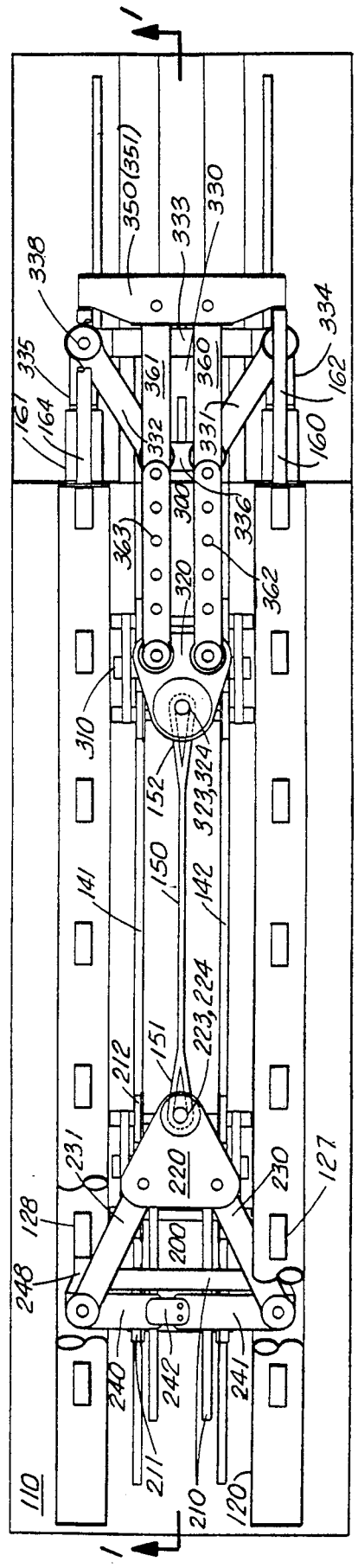
FIG. 2 is a top view of the preferred embodiment of the apparatus of the present invention.
Figure 9:
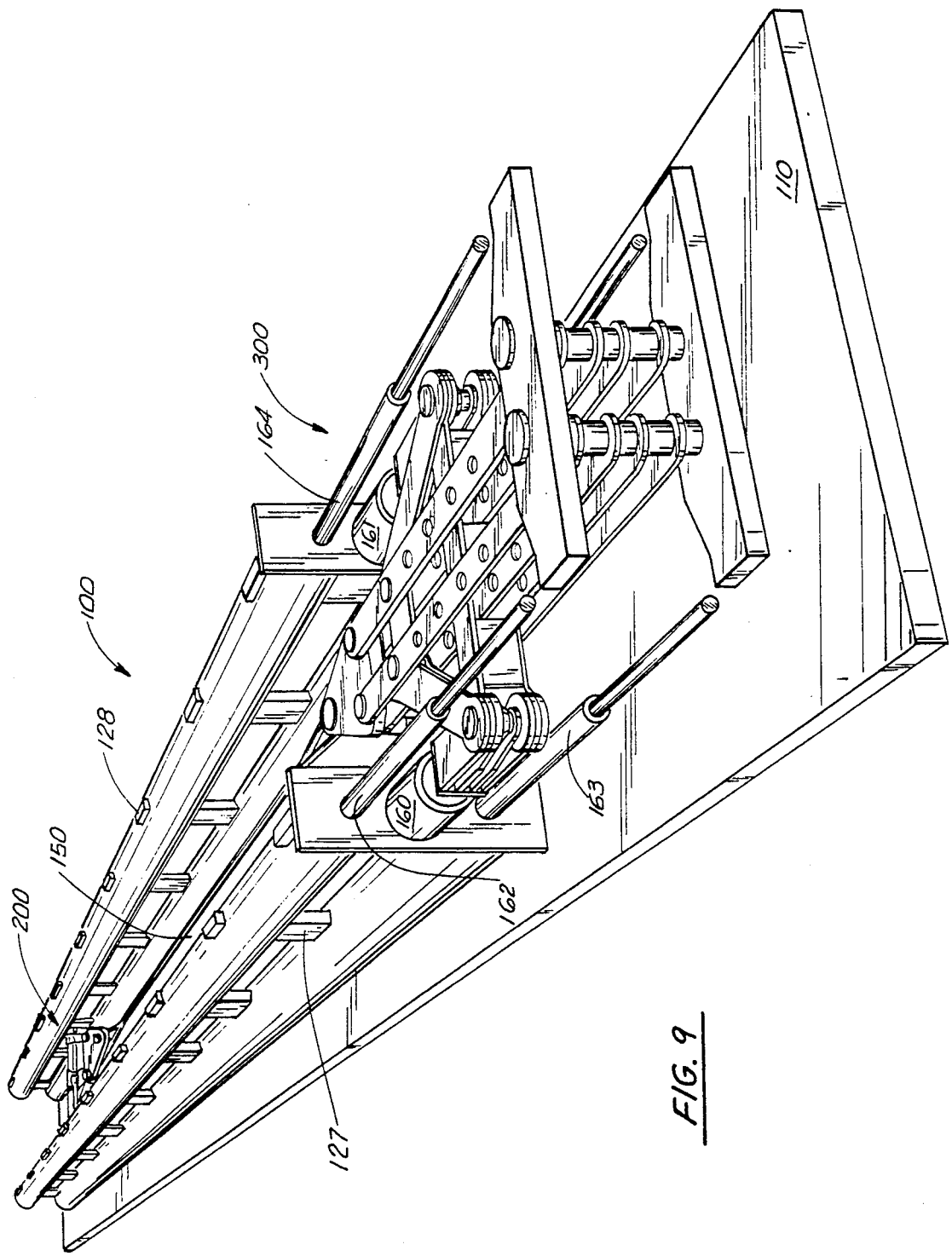
FIG. 9 is a top fragmentary view of the preferred embodiment of the apparatus of the present invention.

A pair of spaced apart and generally parallel rails 141, 142 define runway 140 upon which moves a pair of truss members. A first movable truss 200 provides undercarriage 210 with a plurality of wheels 211, 212. In FIGS. 1 and 2, an elongated tensile Wire rope sling 150 is being tested, the sling 150 providing opposed loop ends in the form of lifting eyes 151, 152. It should be understood that the sling 150, With its lifting eye portions 151, 152 is a commercially available sling member which is commonly used in the lifting of heavy objects. It is supplied in various lengths and diameters, giving each sling 150, its lifting capability and load carrying capability which can approach many hundreds of tons in very large slings.

First movable truss 200 provides connector 220 that includes a pair of spaced apart parallel plates 221, 222. Each plate 221, 222 provides respectively an opening 223, 224. A removable pin 225 is attachable to the plates 221, 222 at the openings 223, 224. The movable truss 200 includes tension arms 230, 231 and compression arms 240, 241 which are pivotally connected at pivot pins 250, 251, 252 and 253.

A lock 242 is used to affix the compression arms 240, 241 together in the aligned position shown in FIG. 7. Lock 242 includes a pair of openings 243, 244 attached to compression arm 240 and lock member 242. A lock pin 246 is inserted through the openings 244, 245 when the compression arms 240, 241 are aligned end to end as shown in FIG. 7. A pivotal, pinned connection 243 is provided between the lock 242 and compression member 241.

First movable truss 200 carries a pair of spaced apart bearing plates 247, 248 that are oriented about ninety degrees (90°) with respect to members 240, 241 as seen in FIGS. 7 and 8. In testing position, these bearing plates 247, 248 engage and bear against one of the plurality of left or right box vertically extending girder stop members 127, 128 as seen in FIG. 2. Vertical pipe members 213, 214 are used for forming a structural interface between the under carriage portion of first movable truss 200 and the upper portion thereof including the plates 221, 222 and the compression and tension arms 230, 231 and 241, 242.

In FIGS. 1, 2, 5 and 6 there is seen a second movable truss 300 which is a powered truss. The powered truss 300 includes undercarriage 310 having a plurality of wheels 311 and skates 312, upwardly extending vertical pipe supports 313, 314, connector 320 and a pair of spaced apart plates 321, 322. Pin 325 forms a connection with eye 152 of sling 150 as seen in FIG. 2. Openings 323, 324 in the plates 321, 322 accommodate pin 325. Bearing plates 334, 335 of truss 300 provide contact for the main load truss 330 with the high load capacity, short stroke jacks 160, 161. Tension arms 331A-D, 332A-D and compression arm 333 form a generally triangular configuration of the main load truss 330 that is similar in configuration to the first truss 200.

A short transverse tension arm 336A-B forms a connection between tension arms 331A-D, 332A-D while providing openings 340, 341 to allow for load transfer pins that connect to longitudinal tension arms 361A-D and 360A-D. Pinned connections 337, 338 are provided at the rear of the main load truss 330, defining pinned connections between the tension arms 331, 332 and the compression arm 333.

Tension arms 360A-D, 361A-D join connector plates 321, 322 with back beams 350-351. Each tension arm 360A-D, 361 A-D is provided with a plurality of spaced adjustment openings 362, 363 respectively. The back beams 350, 351 provide two pairs of spaced apart left and right bearing surfaces 352-355 which engage first pairs of hydraulic rams 162-165. The bearing plates 334, 335 engage a second pair of hydraulic rams 160, 161. In this manner, the rams 162-165 and 160, 161 can be used alternatively to move the entire movable truss 300 in a direction away from the truss 200 when truss 200 is anchored at a desired position using bearing plates 247, 248 to bear against box girder stop members 127, 128.

While the rams 162-165 are moving back beams 350, 351 in a direction away from the first movable truss 200, the position of moveable truss 300 upon rails 141, 142 can be adjusted until the desired openings 362, 363 of tension arms 360, 361 are aligned with load transfer openings 340-341 such as when the sling 150 has been stretched a desired amount, or to a desired loading value. At that time, the openings 340, 341 are then pinned with load transfer pins through desired openings 362, 363, and the second pair of rams 160, 161 engage the bearing plates 334, 335 so that loading to higher load values can continue. Thus, the first rams 162-165 can be of a lower capacity, but with a much greater length of stroke or travel. This would allow most of the slack to be taken out of the sling 150 being tested at a relatively low load value, and most of the preliminary stretching accommodated using the smaller rams 162-165.

The second set of rams 160, 161 can be made very powerful but with a shorter stroke, or travel, so that the upper end of the load range would be taken over by the second set of rams 160, 161. This adjustability, and the optional use of two sets of rams affords great latitude in the testing of a huge number of load elements notwithstanding the length of the particular member nor its rated load capacity, as well as speed and efficiency in the lower capacity range.

The Table 1 below lists the part number and its description for each of the parts used in the drawing figures and in the written specification.

TABLE 1

| PART NO. | PARTS LIST PART DESCRIPTION |
| --- | --- |
| 100 | testing apparatus |
| 110 | pad foundation |
| 120 | frame |
| 121 | left side of frame |
| 122 | right side of frame |
| 123 | compression member |
| 124 | compression member |
| 125 | compression member |
| 126 | compression member |
| 127 | left box girder stops |
| 128 | right box girder stops |
| 140 | runway |
| 141 | rails |
| 142 | rails |
| 150 | sling |
| 151 | lifting eye |
| 152 | lifting eye |
| 160 | high cap./short stroke ram |
| 161 | ram |
| 162 | low cap./long stroke ram |
| 163 | ram |
| 164 | ram |
| 165 | ram |
| 200 | first movable truss |
| 210 | under carriage |
| 211 | wheels |
| 212 | wheels |
| 213 | pipe |
| 214 | pipe |
| 220 | connector |
| 221 | plate |
| 222 | plate |
| 223 | opening |
| 224 | opening |
| 225 | pin (removable) |
| 230A,B | tension arms |
| 231A,B | tension arms |
| 240 | compression arm |
| 241 | compression arm |
| 250 | pivot pin |
| 251 | pivot pin |
| 252 | pivot pin |
| 253 | pivot pin |
| 242 | lock |
| 243 | pivot pin |
| 244 | openings |
| 245 | openings |

TABLE 1-continued

| PART NO. | PARTS LIST PART DESCRIPTION |
| --- | --- |
| 246 | lock pin |
| 247 | bearing plate |
| 248 | bearing plate |
| 300 | second movable truss (powered) |
| 310 | under carriage |
| 311 | wheel |
| 312 | skates |
| 313 | pipe support |
| 314 | pipe support |
| 320 | connector |
| 321 | plate |
| 322 | plate |
| 323 | openings |
| 324 | openings |
| 325 | pin |
| 330 | main load truss |
| 331A-D | tension arms |
| 332A-D | tension arms |
| 333 | compression arm |
| 334 | bearing plate |
| 335 | bearing plate |
| 336A,B | transverse tension arms |
| 337 | pinned connection |
| 338 | pinned connection |
| 350 | back beam |
| 351 | back beam |
| 352 | bearing surface |
| 353 | bearing surface |
| 354 | bearing surface |
| 355 | bearing surface |
| 360A-D | longitudinal tension arm |
| 361A-D | longitudinal tension arm |
| 362 | adjustment openings |
| 363 | adjustment openings |

Because many varying and different embodiments may be made within the scope of the invention concept herein taught, and because many modifications may be made in the embodiments herein detailed in accordance with the descriptive requirement of the law, it is to be understood that the details herein are to be interpreted an illustrative and not in a limiting sense.

What is claimed as invention is:

1. A load testing apparatus for testing lifting accessories, comprising:
   a) an underlying support base;
   b) an elongated frame mounted upon the support base and having a longitudinal axis;
   c) a runway that extends along at least a portion of the frame;
   d) a first carriage movably supported during use above the runway;
   e) a second carriage movably supported during use above the runway;
   f) each carriage having means for anchoring the carriage to the frame;
   g) means for connecting a test specimen to each carriage;
   h) first power means for preliminarily powering at least one carriage to move with respect to the other when specimen to be tested is connected between the carriages;
   i) second power means for secondarily powering one carriage to move with respect to the other when a specimen to be tested is connected between the carriages, and enabling the specimen to be tested in a higher loading range than the loading range that can be exerted on the accessory by the first power means; and
   j) wherein at least one of the power means is positioned to apply force to a carriage at spaced-apart positions on generally opposite sides of the runway.

2. The apparatus of claim 1 wherein the base is a reinforced concrete slab.

3. The apparatus of claim 1 wherein the frame has left and right side frame portions.

4. The apparatus of claim 3 wherein at least a part of the runway is positioned between the left and right frame portions.

5. The apparatus of claim 1 wherein the runway comprises a pair of parallel rails.

6. The apparatus of claim 5 wherein at least one of the carriages is wheeled and adapted to roll upon the rails.

7. The apparatus of claim 6 wherein the frame comprises left and right frame portions that are parallel to the rails.

8. The apparatus of claim 1 wherein the frame has a plurality of longitudinally spaced stops, and one of the carriages has means for anchoring the carriage to the frame at the stops.

9. A load testing apparatus for testing lifting accessories, comprising:
   a) an underlying support base;
   b) an elongated frame mounted upon the support base and having a longitudinal axis;
   c) a runway that extends along at least a portion of the frame;
   d) a first carriage movably mounted on the runway;
   e) a second carriage movably mounted on the runway;
   f) each carriage having means for anchoring the carriage to the frame;
   g) means for connecting a test specimen to each carriage;
   h) first power means for preliminarily powering at least one carriage to move with respect to the other when specimen to be tested is connected between the carriages;
   i) second power means for secondarily powering one carriage to move with respect to the other when a specimen to be tested is connected between the carriage, and enabling the specimen to be tested in a higher loading range than the loading range than can be exerted on the accessory by the first power means; and
   j) wherein at least one of the carriages has bearing members that fold between engaged and retracted positions that enable the carriage to anchor to the frame in the engaged position, and to freely travel with respect to the frame in the retracted position.

10. A load testing apparatus for testing lifting accessories, comprising:
    a) an underlying support base;
    b) an elongated frame mounted upon the support base and having a longitudinal axis and left and right side portions;
    c) a runway that extends along at least a portion of the frame and between the left and right side portions;
    d) a first carriage movably mounted on the runway;
    e) a second carriage movably mounted on the runway;
    f) each carriage having means for anchoring the carriage to both the left and right sides of the frame;
    g) means for connecting a test specimen to each carriage;

h) power means for powering at least one carriage to move with respect to the other when the specimen to be tested is connected between the carriages; and i) wherein at least one of the carriages defines a collapsible truss, so that the carriage can move along the runway when the truss is collapsed.

11. The apparatus of claim 10 wherein the base is a reinforced concrete slab.

12. The apparatus of claim wherein the collapsible truss extends to a width of at least three feet has left and right side frame portions.

13. The apparatus of claim 12 wherein the frame has openings and the truss extends into openings in the frame when expanded.

14. The apparatus of claim 13 wherein the runway comprises a pair of parallel rails.

15. The apparatus of claim 14 wherein at least one of the carriages is wheeled and adapted to roll upon the rails.

16. The apparatus of claim 15 wherein the frame comprises left and right frame portions that are parallel to the rails.

17. The apparatus of claim 16 wherein the frame has a plurality of longitudinally spaced stops, and one of the carriages has means for anchoring the carriage to the frame at the stops.

18. The apparatus of claim 17 wherein at least one of the carriages has bearing members that fold between engaged and retracted positions that enable the carriage to anchor to the frame in the engaged position, and to freely travel with respect to the frame in the retracted position.

19. The apparatus of claim 13 wherein the frame is comprised of longitudinally spaced and vertically extending frame members separated by openings.

20. The apparatus of claim 19 wherein the left and right frame members each having longitudinally spaced and vertically extending frame members separated by openings.

21. The apparatus of claim 10 wherein one of the carriages includes a truss that is triangularly shaped when in testing positions.

22. A load testing apparatus for testing lifting accessories, comprising:

a) an underlying support base;
b) an elongated frame mounted upon the support base and having a longitudinal axis;
c) a runway that extends along at least a portion of the frame;
d) a first carriage movably mounted on the runway;
e) a second carriage movably mounted on the runway;
f) each carriage having means for anchoring the carriage to the frame;
g) means for connecting a test specimen to each carriage;
h) first power means for preliminarily powering at least one carriage to move with respect to the other when specimen to be tested is connected between the carriages;
i) second power means for secondarily powering one carriage to move with respect to the other when a specimen to be tested is connected between the carriage, and enabling the specimen to be tested in a higher loading range than the loading range than can be exerted on the accessory by the first power means; and
j) wherein one of the carriages includes a truss that is triangularly shaped when in testing positions.

* * * * *